United States Patent
Hilliard, Jr. et al.

(10) Patent No.: US 8,015,860 B2
(45) Date of Patent: Sep. 13, 2011

(54) METHOD OF MEASURING DEPOSITION ONTO A SUBSTRATE

(75) Inventors: Peter R. Hilliard, Jr., Far Hills, NJ (US); Joseph R. Knorr, Edison, NJ (US)

(73) Assignee: Colgate-Palmolive Company, New York, NY (US)

( * ) Notice: Subject to any disclaimer, the term of this patent is extended or adjusted under 35 U.S.C. 154(b) by 524 days.

(21) Appl. No.: 12/160,807

(22) PCT Filed: Jun. 24, 2008

(86) PCT No.: PCT/US2008/067991
§ 371 (c)(1),
(2), (4) Date: Jul. 14, 2008

(87) PCT Pub. No.: WO2009/117013
PCT Pub. Date: Sep. 24, 2009

(65) Prior Publication Data
US 2010/0212410 A1    Aug. 26, 2010

Related U.S. Application Data

(63) Continuation of application No. PCT/US2008/057814, filed on Mar. 21, 2008.

(51) Int. Cl.
*G01N 5/02* (2006.01)

(52) U.S. Cl. .......................................... 73/74
(58) Field of Classification Search ................. None
See application file for complete search history.

(56) References Cited

U.S. PATENT DOCUMENTS 3,859,227 A * 1/1975 Dwyer ........................ 516/41

FOREIGN PATENT DOCUMENTS

| GB | 2 317 932 A | | 4/1998 |
|---|---|---|---|
| JP | 06 183907 A | | 7/1994 |
| JP | 06 194290 A | | 7/1994 |
| JP | 06183907 A | * | 7/1994 |
| JP | 2000 234950 A | | 8/2000 |
| JP | 2000234950 A | * | 8/2000 |

OTHER PUBLICATIONS

Abstract for JP 2000 234950 A (Shintoo Fine KK) (Aug. 29, 2000).
Abstract for JP 06 183907 A Hakuto KK (Jul. 5, 1994).
Abstract for JP 06 194290 A Hitachi Ltd. (Jul. 15, 1994).
International Search Report PCT/US2008/067991, Dated Dec. 17, 2008.

* cited by examiner

*Primary Examiner* — Hezron Williams
*Assistant Examiner* — Alex Devito
(74) *Attorney, Agent, or Firm* — Michael F. Morgan

(57) ABSTRACT

A method of measuring the deposition of a composition onto a substrate. This information can be used to correlate how the composition will deposit on sanitary ware, such as shower cubicles, baths, and wash basins. The composition can be a liquid personal cleansing composition.

9 Claims, No Drawings

METHOD OF MEASURING DEPOSITION ONTO A SUBSTRATE

CROSS REFERENCE TO RELATED APPLICATIONS

This application is a continuation in part of International Application Serial No. PCT/US2008/57814, filed on 21 Mar. 2008, which is incorporated herein by reference.

BACKGROUND OF THE INVENTION

When developing personal cleansing compositions for use in the shower, bath or sink, it is desired to minimize the amount of cleaning of the composition from the shower, bath, or sink. It is desired for the compositions to deposit as little as possible on a substrate to minimize the cleaning.

To measure the actual deposition of a composition onto sanitary ware would require actual use of the composition. This would require a significant amount of labor and time to have people use compositions in the shower, bath, or sink. It would be desirable to reduce this amount of labor and time.

BRIEF SUMMARY OF THE INVENTION

The present invention relates to a method of measuring the deposition of a composition onto a substrate. This information can be used to correlate how the composition will deposit on sanitary ware, such as shower cubicles, baths, and wash basins.

In particular, the present invention relates to a method for measuring the residue left by a composition on a substrate, the method comprising:
a) providing a substrate;
b) weighing the substrate to obtain an initial weight;
c) providing in a container a mixture comprising a measured amount of water of a desired hardness and a measured amount of a composition to be tested;
d) immersing the substrate in the mixture for a time sufficient to allow the composition to wet the substrate;
e) removing the substrate and allowing excess mixture to drain off of the substrate;
f) drying the substrate; and
g) weighing the substrate to obtain a final weight.

The method may further comprise, between steps b) and c), rinsing and drying the substrate by rinsing the substrate in the following at room temperature: i) tap water; then ii) de-ionized water; then iii) 200 proof ethanol; then iv) reagent grade Acetone; and then air drying the substrate.

The method may further comprise, to provide the mixture in the container in step c),
i) measuring the amount of water of the desired hardness into the container;
ii) inserting a mixer into the container;
iii) adjusting the container and water to a desired temperature;
iv) adding the composition to be tested to form the mixture;
v) mixing the mixture;
vi) optionally adjusting the mixture to a desired temperature; and
vii) stopping mixing.

Optionally, in the immersion step d), if the substrate is not fully immersed in the mixture, the substrate is initially partially immersed and then removed from the mixture, rotated about 180 degrees, and then placed back into the mixture so as to be partially immersed again in the mixture.

Optionally, the method further comprises comparing the initial and final weights to determine the weight of residue adhering to the substrate.

Optionally, the method further comprises determining the unit weight of the residue per unit area of the substrate by dividing the weight of residue by the total surface area of the substrate.

Preferably, the composition is a personal cleansing composition, and the substrate is composed of a material selected from the group consisting of glass, ceramic, porcelain, tile, acrylic, and fiberglass. More preferably, the method is for correlating the amount of residue left by the composition on sanitary ware when the personal cleansing composition is used in a bathroom.

In one embodiment, the invention relates to a method comprising:
a) selecting a substrate of a known initial weight;
b) optionally, rinsing the substrate in the following at room temperature:
   i) tap water;
   ii) de-ionized water;
   iii) 200 proof ethanol;
   iv) reagent grade Acetone;
   v) air drying the substrate; and
   vi) weighing the substrate to obtain the initial weight;
c) measuring an amount of water of a desired hardness into a container;
d) inserting a mixer into the container;
e) adjusting the container and water to a desired temperature;
f) adding a composition to be tested to form a mixture;
g) mixing the mixture;
h) adjusting the mixture to a desired temperature, if needed;
i) stopping mixing;
j) inserting at least 1 substrate into the mixture;
k) allowing the substrate to sit in the mixture for a time sufficient to allow the composition to wet the substrate;
l) optionally, if the substrate is not fully immersed in the mixture, removing and rotating the substrate 180 degrees, followed by placement back in the mixture as described in steps j) and k);
m) removing the substrate and allowing the substrate to drain for a time sufficient for excess mixture to run off of the substrate;
n) placing the substrate into a holder and drying for a sufficient amount of time;
o) weighing the substrate to obtain a final weight;
p) optionally, comparing to the pre-washed weight with the final weight to determine the amount of residue adhering to the substrate;
q) optionally, converting the weight of the residue to mass per area by dividing the mass of residue by the total surface area of the substrate; and
wherein the size of the substrate, the size of the container, the amount of the water, and the amount of the composition are selected so that substrate can fit into the container and be immersed in the water and the composition.

DETAILED DESCRIPTION OF THE INVENTION

As used throughout the present disclosure, ranges are a shorthand for describing each and every value that is within the range. Any value within the range can be selected as the terminus of the range. In addition, all references cited in the present disclosure are hereby incorporated by reference in their entireties. In the event of any conflict between a definition in the present disclosure and that of a cited reference, the present disclosure controls.

As used throughout this specification and claims, except as noted below in the examples, the amount of material listed is the active weight of the material.

As used throughout, "room temperature" refers to 23° C.±1.

The method for measuring the residue left by a composition on a substrate may comprise:
a) selecting a substrate of a known initial weight;
b) optionally, rinsing the substrate in the following at room temperature:
   i) tap water;
   ii) de-ionized water;
   iii) 200 proof ethanol;
   iv) reagent grade Acetone;
   v) air drying the substrate; and
   vi) weighing the substrate to obtain the initial weight;
c) measuring an amount of water of a desired hardness into a container;
d) inserting a mixer into the container;
e) adjusting the container and water to a desired temperature;
f) adding a composition to be tested to form a mixture;
g) mixing the mixture;
h) adjusting the mixture to a desired temperature, if needed;
i) stopping mixing;
j) inserting at least 1 substrate into the mixture;
k) allowing the substrate to sit in the mixture for a time sufficient to allow the composition to wet the substrate;
l) optionally, if the substrate is not fully immersed in the mixture, removing and rotating the substrate 180 degrees, followed by placement back in the mixture as described in steps j) and k);
m) removing the substrate and allowing the substrate to drain for a time sufficient for excess mixture to run off of the substrate;
n) placing the substrate into a holder and drying for a sufficient amount of time;
o) weighing the substrate to obtain a final weight;
p) optionally, comparing to the pre-washed weight with the final weight to determine the amount of residue adhering to the substrate;
q) optionally, converting the weight of the residue to mass per area by dividing the mass of residue by the total surface area of the substrate; and
wherein the size of the substrate, the size of the container, the amount of the water, and the amount of the composition are selected so that substrate can fit into the container and be immersed in the water and the composition.

The size of the substrate and container can be selected to be any desired size. For laboratory testing, typical laboratory sized equipment can be selected. In one embodiment, the substrate can be a standard glass slide, and the container can be a beaker.

The substrate can be any desired substrate. For comparison to bathroom surfaces, the substrate can be any surface found in a bathroom. Examples include, glass, ceramic, porcelain, tile, acrylic, or fiberglass. If it is desired to determine the residue left on a particular substrate, that substrate can be used. For comparing the residue left by different compositions, any type of substrate can be used for comparative purposes. When selecting a substrate, all of the surfaces should be the same because all surfaces will be immersed in the composition to the same depth for testing. Tile, for example, typically has a glazed finish on one surface and clay on an opposite surface. Tile should be provided that has the same glazed finish on all surfaces. For convenience, glass laboratory slides can be selected as the substrate.

Optionally, the substrate can be rinsed prior to use to provide a clean substrate. In one embodiment, the rinsing is done with each of the following materials in succession: tap water, deionized water (generally, less than about 1 μSem), 200 proof ethanol, and reagent grade acetone. After rinsing, the substrate is allowed to dry. Optionally, the substrate can be dried between each rinse material.

The water hardness of water used to dilute the composition can be selected to be any desired hardness. By selecting different water hardness, the effect of water hardness on the deposition onto substrates can be measured.

Mixing can be done with any type of mixer that can mix the contents of the container size selected. In some embodiments, the mixer can be selected to be a magnetically driven stir bar or an impeller driven mixer.

The temperature of the composition can be changed to be measured at any desired temperature. If the deposition at bathing temperatures is desired to be measured, then the temperature can be selected to be any temperature that a person would use for bathing. In some embodiments, the temperature is about 25° C. to about 50° C. In one embodiment, human body temperature, about 37° C., can be selected. In certain embodiments, the adjusting of the temperature is not necessary if the temperature is at the desired temperature.

The substrate can be fully immersed into the mixture, or the substrate can be partially immersed. Partial immersion can be used to simulate a shower environment. To simulate a shower environment, the substrate can be inserted at any desired angle into the mixture. The selection of the angle is to maximize the area of the substrate in the mixture. In some embodiments, the angle is about 10 to about 30°. In some embodiments, the substrate is not to be directly parallel with the sides of the container. In some embodiments, approximately ⅔ of the slide's length will be submerged using this technique to simulate the partial exposure to liquid and air as would be present in a shower environment. If more than one substrate is used, they should not touch each other.

The substrate can be inserted with any desired article that can hold the substrate. In some embodiments, the holder can be tweezers, pliers, or clamps.

The substrate can remain immersed in the mixture for any desired length of time. The time can be selected to be the amount of time for bathing. In some embodiments, the amount of time can be about 1 minute to about 30 minutes. In certain embodiments, the time can be selected to be about 10 minutes.

After the substrate has been immersed for the desired amount of time, the substrate is removed and excess mixture is allowed to drain off of the substrate. In one embodiment, the substrate is held at an angle to allow the mixture to drain to one corner and drip off. This can be followed by touching the corner of the substrate to the edge of the container, without disturbing the surfaces of the substrate, to remove excess mixture.

The substrate is then placed into a holder to allow the substrate to dry. The time is selected to be a time that allows for the mixture to dry. In one embodiment, the amount of time is about 24 hours. The drying can be done by air drying to more closely approximate the conditions after bathing. Optionally, the drying can be done in a heated environment at a temperature below any selected bathing temperature, which can be less than about 50° C. The temperature should not be higher than a maximum temperature used for bathing so as to prevent solids that would be present after bathing from being volatilized away or flowing off the substrate.

After drying, the substrate is weighed to obtain a final weight. The amount of material deposited on the substrate is calculated by subtracting the initial weight from the final weight.

The mass per area can be determined by dividing the mass by the total surface area of the substrate. If more than one substrate was tested, additional statistical analysis, such as the mean and standard deviation, can be calculated.

Example 1

In this Example, the tendency of a composition (exemplified by Compositions 1 to 4) to have a low residue deposition onto a glass surface, representing a surface of sanitary ware, was investigated, and compared to a currently commercially available moisturizing bodywash (Composition X) which exhibited a significantly higher residue deposition. Composition 1 and Composition X were tested using water at two different water hardness levels.

In particular, glass slides were treated in accordance with the following method with various body cleansing products to be tested:

Method for Residue Deposition on Glass for Liquid Body Cleansing Products.

1. Scribe glass slides to uniquely identify them for the test. Slide dimensions should be approximately 7.56 cm×2.49 cm×0.1 cm and weigh approximately 4.5 g.
2. Rinsed pre-washed slides in the following at room temperature in sequence:
   a. Tap water
   b. De-ionized water (less than about 1 μSem)
   c. 200 proof ethanol
   d. Reagent grade Acetone.
3. Weigh out 85 g of water of the desired hardness into a 150 ml Pyrex beaker. (In this case either 100 or 200 ppm, although other levels of water hardness could be used).
4. Add a Teflon (polytetrafluoroethylene) coated stir bar.
5. Heat the water in the beaker to 37° C. with the stir bar set to 350 rpm with a hot plate that can be controlled with an attached thermocouple.
6. Remove from the hot plate and add 15 g of product to be tested.
7. Return to the hot plate and continue to maintain temperature at 37° C.
8. Stir with the stir bar at 450 rpm for 6 minutes.
9. Stop stirring and turn off the hot plate, but keep the beaker on the hot plate. During the rest of the procedure the temperature should drop no lower than about 33° C.
10. Place 4 pre-weighed glass slides at an arbitrary angle (generally about 10 to about 30°) in the solution so as not to be touching each other, and not to be directly parallel with the sides of the beaker. This is to maximize the area of the slides exposed to the liquid. In addition, approximately ⅔ of the slide's length will be submerged using this technique to simulate partial exposure to liquid as would be present in a shower environment.
11. Allow the slides to sit in the solution for ten minutes.
12. Remove (lift) the slides out of the solution with tweezers and rotate 180 degrees, followed by placement back in the solution as described above.
13. Allow the slides to sit in the solution for an additional ten minutes.
14. Remove (lift) the slides out of the solution with tweezers and allow the slides to drain for approximately 5 seconds to one corner, followed by touching the corner of the slide to the edge of the beaker to remove excess fluid without substantially disturbing the surfaces of the slides.
15. Place the slide into a slide holder with a paper absorbent bottom to minimize disturbance of the slide surfaces and allow to air dry for at least 24 hours at room temperature.
16. Weigh the slides and compare to the pre-washed weight to determine the amount of residue adhering to the slides.
17. Convert the weight of the residue to mg/cm$^2$ by dividing the mg of residue by the total surface area of the slide (approximately 39.7 cm$^2$).
18. Calculate the mean mg/cm$^2$ and standard deviation of each product treatment, perform statistical analyses using the student t-test.

The results are summarized in Table 1.

TABLE 1

| Formula | % Petrolatum/ Emollients in formula | Water Hardness (ppm) | Petrolatum Deposition on Glass mg/cm$^2$ | StDev |
|---|---|---|---|---|
| Composition 1 | 5 | 100 | 0.62 | 0.19 |
| Composition 1 | 5 | 200 | 0.64 | 0.22 |
| Composition 2 | 1.5 | 200 | 0.17 | 0.06 |
| Composition 3 | 5 | 200 | 0.59 | 0.21 |
| Composition 4 | 8 | 200 | 0.87 | 0.24 |
| Composition X | Estimated 48% | 100 | 2.44 | 0.52 |
| Composition X | Estimated 48% | 200 | 2.10 | 1.28 |

The Compositions of 1 to 4 above are summarized in Table 2.

TABLE 2

| Ingredients | Comp. 1 Wt % | Comp. 2 Wt % | Comp. 3 Wt % | Comp. 4 Wt % |
|---|---|---|---|---|
| Deionized Water | 64.29 | 68.78 | 63.73 | 61.58 |
| Glycerin | 2.50 | — | 2.50 | 2.50 |
| Laponite ™ XLG | 0.30 | 0.30 | 0.30 | 0.30 |
| PEG 400 | 0.90 | 0.90 | 0.90 | 0.90 |
| C12-C14 Alcohol EO 2:1 Na sulfate (70%) | 9.37 | 9.37 | 9.37 | 9.37 |
| Aculyn ™ 88 | 4.25 | 4.25 | 4.25 | 4.25 |
| Tetrasodium EDTA (62%) | 0.10 | — | 0.10 | 0.10 |
| Tetrasodium EDTA (39%) | — | 0.23 | — | — |
| DMDM Hydantoin | 0.50 | 0.60 | 0.50 | 0.50 |
| NaOH (50%) | 0.28 | 0.32 | 0.70 | 0.35 |
| Cocoamidopropyl Betaine (30%) | 8.65 | 8.65 | 8.65 | 8.65 |
| PolyQuat 7 | 1.20 | 1.20 | 1.20 | 1.20 |
| Sunflower Oil | 1.50 | 3.00 | 1.50 | 1.00 |
| Petrolatum | 5.00 | 1.50 | 5.00 | 8.00 |
| Maleated Caster Oil (Ceraphyl ™ RMT) | 0.10 | — | 0.10 | 0.10 |
| Fragrance | 0.95 | 0.90 | 0.90 | 0.90 |
| PPG-10 Methyl Glucose Ether | — | — | 0.20 | 0.20 |
| Pigment | 0.70 | — | 0.10 | 0.10 |
| Fruit extract | 0.05 | — | — | — |

The Composition X was the Oil of Olay Ribbons Body Wash product available in commerce from The Procter & Gamble Company, Cincinnati, Ohio, USA which had the following labeled composition: Water, Petrolatum, Sodium Trideceth Sulfate, Mineral Oil, Sodium Lauroamphoacetate, Sodium Chloride, Cocamide MEA, Fragrance. Prunus Amygdalus Dulcis (Sweet Almond) Oil, Hydrolyzed Silk, Guar Hydroxypropyltrimonium Chloride, Glycerin, Citric Acid, DMDM Hydantoin, Acrylonitrile/Methacrylonitrile/Methyl Methacrylate Copolymer, Isopentane, Sodium Benzoate. PEG-90M, Disodium EDTA, Sodium Hydroxide, Red 7.

What is claimed is:

1. A method for measuring the residue left by a composition on a substrate comprising:
   a) providing a substrate;
   b) weighing the substrate to obtain an initial weight;
   c) providing in a container a mixture comprising a measured amount of water of a desired hardness and a measured amount of a composition to be tested;
   d) immersing the substrate in the mixture for a time sufficient to allow the composition to wet the substrate;
   e) removing the substrate and allowing excess mixture to drain off of the substrate;
   f) drying the substrate; and
   g) weighing the substrate to obtain a final weight,
   wherein the composition is a personal cleansing composition, and the substrate is composed of a material selected from the group consisting of glass, ceramic, porcelain, tile, acrylic, and fiberglass.

2. The method of claim 1, wherein the method further comprises, between steps b) and c), rinsing and drying the substrate by rinsing the substrate in the following at room temperature:
   i) tap water; then
   ii) de-ionized water; then
   iii) 200 proof ethanol; then
   iv) reagent grade Acetone; and
   then air drying the substrate.

3. The method of claim 1, wherein the method further comprises, to provide the mixture in the container in step c),
   i) measuring the amount of water of the desired hardness into the container;
   ii) inserting a mixer into the container;
   iii) adjusting the container and water to a desired temperature;
   iv) adding the composition to be tested to form the mixture;
   v) mixing the mixture;
   vi) optionally adjusting the mixture to a desired temperature; and
   vii) stopping mixing.

4. The method of claim 1, wherein, in the immersion step d), if the substrate is not fully immersed in the mixture, the substrate is initially partially immersed and then removed from the mixture, rotated about 180 degrees, and then placed back into the mixture so as to be partially immersed again in the mixture.

5. The method of claim 1, wherein the method further comprises comparing the initial and final weights to determine the weight of residue adhering to the substrate.

6. The method of claim 5, wherein the method further comprises determining the unit weight of the residue per unit area of the substrate by dividing the weight of residue by the total surface area of the substrate.

7. The method of claim 1, wherein the method is for correlating the amount of residue left by the composition on sanitary ware when the personal cleansing composition is used in a bathroom.

8. The method of claim 1, wherein the method comprises:
   a. selecting a glass slide having approximate dimensions of 7.56 cm×2.49 cm×0.1 cm and weighing approximately 4.5 g;
   b. rinsing the glass slide in the following at room temperature in sequence:
      i. Tap water,
      ii. De-ionized water (less than about 1 µSem),
      iii. 200 proof ethanol, and
      iv. Reagent grade Acetone;
   c. weighing the glass slide to obtain an initial weight;
   d. weighing 85 g of water of a desired hardness into a 150 ml beaker;
   e. inserting a polytetrafluoroethylene coated stir bar;
   f. heating the water in the beaker to 37° C. with the stir bar set to 350 rpm with a hot plate that can be controlled with an attached thermocouple;
   g. removing the beaker from the hot plate;
   h. adding 15 g of product to be tested;
   i. returning the beaker to the hot plate and continuing to maintain temperature at 37° C.;
   j. stirring with the stir bar at 450 rpm for 6 minutes;
   k. stopping stifling and turning off the hot plate, but keeping the beaker on the hot plate;
   l. during the rest of the method, the temperature should drop no lower than about 33° C.;
   m. placing 4 glass slides processed via steps a) to c) at an angle of 10 to 30° in the solution so as not to be touching each other, and not to be directly parallel with the sides of the beaker, and to a depth to cover ⅔ of the slide's length;
   n. allowing the slides to sit in the solution for ten minutes;
   o. removing the slides out of the solution and rotating 180 degrees, followed by placement back in the solution as described in step m);
   p. allowing the slides to sit in the solution for an additional ten minutes;
   q. removing the slides out of the solution and allowing the slides to drain for approximately 5 seconds to one corner, followed by touching the corner of the slide to the edge of the beaker to remove excess fluid without disturbing the surfaces of the slides;
   r. placing the slides into a slide holder with a paper absorbent bottom to minimize disturbance of the slide surfaces and allow to air dry for at least 24 hours at room temperature; and
   s. weighing the slides to obtain a final weight.

9. The method of claim 8, further comprising:
   t. comparing the final weight to the initial weight to determine an amount of residue adhering to the slides;
   u. converting the weight of the residue to mg/cm$^2$ by dividing the weight of residue by the total surface area of the slide;
   v. calculating a mean mg/cm$^2$ and standard deviation of each product treatment.

* * * * *